(12) United States Patent
Steiner et al.

(10) Patent No.: US 7,658,721 B2
(45) Date of Patent: Feb. 9, 2010

(54) SUBLINGUAL DRUG DELIVERY DEVICE

(75) Inventors: Solomon S. Steiner, Mount Kisco, NY (US); Craig Brown, Sherman, CT (US); Roderike Pohl, Sherman, CT (US); Trent Poole, South Amherst, MA (US); Erik Steiner, New York, NY (US)

(73) Assignee: Biodel Inc., Danbury, CT (US)

( * ) Notice: Subject to any disclaimer, the term of this patent is extended or adjusted under 35 U.S.C. 154(b) by 538 days.

(21) Appl. No.: 11/037,737

(22) Filed: Jan. 18, 2005

(65) Prior Publication Data

US 2005/0155601 A1 Jul. 21, 2005
US 2008/0047550 A2 Feb. 28, 2008

Related U.S. Application Data

(60) Provisional application No. 60/537,266, filed on Jan. 16, 2004.

(51) Int. Cl.
*A61M 37/00* (2006.01)
*A61M 15/00* (2006.01)
*A61M 16/10* (2006.01)
*A61M 16/00* (2006.01)
*A61M 11/00* (2006.01)

(52) U.S. Cl. ............... 604/24; 128/203.12; 128/203.19; 128/200.22

(58) Field of Classification Search ............ 128/203.15, 128/203.19, 203.21, 200.14, 200.17, 200.18, 128/200.21, 200.22, 203.12; 604/21, 24
See application file for complete search history.

(56) References Cited

U.S. PATENT DOCUMENTS 3,921,637 A 11/1975 Bennie et al.
4,196,196 A 4/1980 Tiholiz (Continued)

FOREIGN PATENT DOCUMENTS

DE 247684 7/1987

(Continued)

OTHER PUBLICATIONS

Aungst & Rogers, "Site dependence of absorption-promoting actions of laureth-9, Na salicylate, Na2EDTA, and aprotinin on rectal, nasal, and buccal insulin delivery", *Pharm. Res.*, 5(5):305-308 (1988).

(Continued)

*Primary Examiner*—Justine R Yu
*Assistant Examiner*—Kristen C Matter
(74) *Attorney, Agent, or Firm*—Pabst Patent Group LLP (57) ABSTRACT

A drug delivery device that aerosolizes a dry powder formulation so that it forms a fine coating in the oral cavity and, more specifically in the sublingual region of the oral cavity is described herein. In the preferred embodiment, the device contains five main parts: (i) a compressed gas canister, (ii) a dispenser body (also referred to herein as the main housing ), (iii) a means for storing one or more doses of a drug formulation, (iv) a means for releasing a dose of the drug formulation such as a gas canister or spring piston and (v) a mouthpiece. Preferred configurations include circular, tubular, and rectangular. The means for storing the drug formulation may be configured to separately store one or more materials. In one embodiment, the means for storing the active agent is in the form of one or more drug discs, where the drug discs contain a plurality of blister packs, each storing one dose of the drug formulation. In another embodiment, the means for storing the active agent is a dosage cartridge containing a single dose of the drug formulation. In yet another embodiment, the drug formulation is stored on a ribbon containing a plurality of blister packs, each storing one dose of the drug formulation.

18 Claims, 10 Drawing Sheets

U.S. PATENT DOCUMENTS

| | | | |
|---|---|---|---|
| 4,211,769 | A | 7/1980 | Okada et al. |
| 5,388,572 | A | 2/1995 | Mulhauser et al. |
| 5,474,978 | A | 12/1995 | Bakaysa |
| 5,534,488 | A | 7/1996 | Hoffmann |
| 5,645,050 | A | 7/1997 | Zierenberg et al. |
| 5,650,486 | A | 7/1997 | Felippis |
| 5,653,987 | A | 8/1997 | Modi et al. |
| 5,672,359 | A | 9/1997 | Digenis |
| 5,746,227 | A * | 5/1998 | Rose et al. ............... 131/270 |
| 5,819,726 | A | 10/1998 | Rubsamen et al. |
| 5,849,322 | A | 12/1998 | Ebert et al. |
| 5,888,477 | A | 3/1999 | Gonda |
| 5,898,028 | A | 4/1999 | Jensen |
| 5,929,027 | A | 7/1999 | Takama et al. |
| 5,964,417 | A | 10/1999 | Amann et al. |
| 6,116,238 | A * | 9/2000 | Jackson et al. ......... 128/203.15 |
| 6,123,068 | A * | 9/2000 | Lloyd et al. ............ 128/200.24 |
| 6,125,844 | A * | 10/2000 | Samiotes ............... 128/200.23 |
| 6,264,981 | B1 | 7/2001 | Zhang |
| 6,310,038 | B1 | 10/2001 | Havelund |
| 7,192,919 | B2 | 3/2002 | Tzannis |
| 6,465,425 | B1 | 10/2002 | Tracy |
| 6,652,885 | B2 | 11/2003 | Steiner et al. |
| 6,676,931 | B2 | 1/2004 | Dugger |
| 6,748,946 | B1* | 6/2004 | Rand et al. ............ 128/203.15 |
| 6,941,948 | B2* | 9/2005 | Staniforth et al. ...... 128/203.21 |
| 6,949,258 | B2 | 9/2005 | Zhang et al. |
| 6,960,561 | B2 | 11/2005 | Boderke |
| 7,089,934 | B2* | 8/2006 | Staniforth et al. ...... 128/203.15 |
| 7,249,687 | B2* | 7/2007 | Anderson ...................... 221/5 |
| 2001/0039260 | A1 | 11/2001 | Havelund |
| 2002/0170560 | A1* | 11/2002 | Young et al. .......... 128/203.15 |
| 2002/0198140 | A1 | 12/2002 | Havelund |
| 2003/0015191 | A1* | 1/2003 | Armstrong et al. ..... 128/200.21 |
| 2003/0064097 | A1 | 4/2003 | Patel et al. |
| 2003/0172924 | A1* | 9/2003 | Staniforth et al. ...... 128/200.14 |
| 2003/0183229 | A1 | 10/2003 | Smith et al. |
| 2004/0216738 | A1* | 11/2004 | Edwards et al. ........ 128/203.21 |
| 2005/0005934 | A1* | 1/2005 | Harvey ................. 128/203.15 |
| 2005/0016533 | A1* | 1/2005 | Schuler et al. ......... 128/203.15 |
| 2005/0150492 | A1* | 7/2005 | Dunkley et al. ........ 128/203.21 |
| 2005/0203001 | A1 | 9/2005 | Arbit et al. |
| 2006/0048780 | A1* | 3/2006 | Burr et al. ............. 128/203.15 |
| 2006/0067891 | A1* | 3/2006 | Modi .......................... 424/46 |
| 2007/0062525 | A1* | 3/2007 | Bonney et al. ......... 128/203.21 |
| 2007/0134279 | A1 | 6/2007 | Stern |
| 2007/0155654 | A1 | 7/2007 | Langkjaer |

FOREIGN PATENT DOCUMENTS

| | | |
|---|---|---|
| GB | 2 069 502 | 8/1981 |
| WO | WO 91/08764 | 6/1991 |
| WO | WO 96/10996 | 4/1996 |
| WO | WO 96/36352 | 11/1996 |
| WO | WO 97/33531 | 9/1997 |
| WO | WO 97/49386 | 12/1997 |
| WO | WO 98/42367 | 10/1998 |
| WO | WO 98/42368 | 10/1998 |
| WO | WO 98/42749 | 10/1998 |
| WO | WO 2004/080401 | 9/2004 |
| WO | WO 2007/047948 | 4/2007 |

OTHER PUBLICATIONS

Brange, et al., Chemical stability of insulin 1: hydrolytic degradation during storage of pharmaceutical preparations, *Pharm. Res.*, 9:715-726 (1992).

De Sousa, et al., "Biocompatibility of EDTA, EGTA and citric acid", *Braz. Dent. J.*, 16:3-8 (2005).

Kang, et al., "Subcutaneous insulin absorption explained by insulin's physiochemical properties", *Diabetes Care*, 14:942-948 (1991).

Keowmaneechai, et al., "Influence of EDTA and citrate on physiochemical properties of whey protein-stabilized oil-in-water emulsions containing $CaCl_2$ ", *J. Agricultural and Food, Chemistry*, 50:7145-7153 (2002).

Klauser, et al., "Mixtures of human intermediate and human regular insulin in type 1 diabetic patients", *Diabetes Res. and Clin. Practice*, 5:185-190 (1988).

Monch & Dehnen, "High-performance liquid chromatography of polypeptides and proteins on a reversed-phase support", *Journal of Chromatography*, 147:415-418 (1978).

Prabhu, et al., "A study of factors controlling dissolution kinetics of zinc complexed protein suspensions in various ionic species", *Int. J. Pharm.*, 217(1-2):71-78 (2001).

Quinn, et al., "Minimizing the aggregation of insulin solutions", *J. Pharmaceutical Sci.*, 72:1472-1473 (1983).

Szepesy & Horvath, "Specific salt effects in hydrophobic interaction chromatography of proteins", *Chromatographia*, 26:13-18 (1988).

Todo, et al., "Effect of additives on insulin absorption from intracheally administered dry powders in rats", *Int J. Pharmaceutics*, 220:101-110 (2001).

* cited by examiner

PRIOR ART

SUBLINGUAL DRUG DELIVERY DEVICE

CROSS-REFERENCE TO RELATED APPLICATIONS

This application claims priority to U.S. Ser. No. 60/537,266, entitled "Sublingual Drug Delivery Device" to Solomon S. Steiner, Craig Brown, Roderike Pohl, Trent Poole, and Erik Steiner, filed Jan. 16, 2004.

FILED OF THE INVENTION

The present invention relates to devices for oral, buccal and/or sublingual drug delivery.

BACKGROUND OF THE INVENTION

Absorption of any molecule, such as a nutrient or pharmaceutical agent, from the oral cavity and more specifically from the lingual and sub-lingual regions involves a different route than absorption of molecules through the gastrointestinal tract. Molecules absorbed from the stomach and small intestines of the gastro-intestinal tract are collected in the hepatic portal drainage system and go directly to the liver where they are exposed to a variety of enzymes which degrade many therapeutics and nutrients, including peptides, proteins and oligonucleotides. In contrast, molecules absorbed from the oral, lingual and sub-lingual regions go directly into the systemic circulation, bypassing the hepatic portal system and avoiding initial exposure to the enzymes in the gastrointestinal tract. The oral cavity is a far gentler environment for many molecules, especially peptides and proteins, compared to the harsh acidic and peptide lysing environment of the stomach and intestines. Furthermore, the underside and base of the tongue, as well as the base of the oral cavity beneath the tongue, are highly variegated ad vascularized, containing capillaries close to the surface, which presents a considerable surface area to allow rapid absorption of a desired drug or nutrient.

For the above reasons, the oral cavity and more specifically, the lingual and sub-lingual regions of the oral cavity, appear to be an idea site for the delivery of many therapeutic and nutritional molecules, including peptides and proteins. However, while a number of drugs have been successfully delivered by this route, there remain a number of problems with this mode of delivery.

One problem with using the oral cavity for drug delivery is due to a patient's automatic swallowing response. A liquid placed in the oral cavity in amounts greater than 200 microliters (µL) will usually elicit a swallowing response, removing the drug to be delivered from the oral cavity and subjecting it to the harsh conditions of the stomach. As a result, most of the drug delivered to the buccal cavity is no longer available for absorption from the oral, lingual and sub-lingual regions. This reduces the bioavailability of the drug.

Attempts have been made to overcome this problem by affixing the drug to a film or other adhesive that adheres to the sublingual space, trapping the drug next to the absorptive surface. However, this approach presents many limitations. For example, a film or patch utilizes only a limited amount of the potential surface area that is available for absorption, which thereby reduces the amount of drug that can be delivered. Additionally, the base of the tongue is irregularly shaped and variegated and as a result standardized patches do not readily adhere to it. Further, an individual who has a foreign substance located under the tongue normally automatically reacts by moving the position of the foreign substance and swallow it.

Therefore it is an object of the invention to provide a device for administering drugs to the oral cavity, particularly the sub-lingual region.

It is a further object of the invention to provide improved bioavailability for oral drug delivery.

BRIEF SUMMARY OF THE INVENTION

A drug delivery device that aerosolizes a dry powder formulation of a therapeutic agent or nutrient and dispenses the formulation so that it forms a fine coating in the oral cavity and, more specifically, in the sublingual region of the oral cavity, has been developed. In the preferred embodiments the device contains five main parts: (i) a compressed gas canister, (ii) a dispenser body (also referred to herein as the main housing), (iii) a means for storing one or more doses of a drug for formulation in the housing, (iv) a means for releasing a dose of the drug formulation and (v) a mouthpiece. In the preferred embodiment, the mouthpiece is configured to deliver the drug to the sublingual region of the oral cavity. Preferred housing configurations include circular, tubular, and rectangular. The means for storing the drug formulation may be configured to separately store one or more materials. In one embodiment, the means for storing the active agent is in the form of one or more drug discs, where the drug discs contain a plurality of blister packs, each storing one dose of the drug formulation. In another embodiment, the means for storing the active agent is a dosage cartridge containing a single dose of the drug formulation. In yet another embodiment, the drug formulation is stored on a ribbon containing a plurality of blister packs, each storing one dose of the drug formulation. In one embodiment, the means for releasing a dose is a gas canister. In another embodiment, the gas canister is replaced with a piston assembly.

The device is used to administer one or more doses by placing the mouthpiece in the mouth and activating the means for releasing a dose. The mouthpiece is then withdrawn from the mouth.

BRIEF DESCRIPTION OF THE DRAWINGS

FIGS. 1A, 1B and 1C are drawings of drug dispensing device having a tubular configuration. FIGS. 1A and 1B are plan views of the device, showing the door to the drug storage means open and closed, respectively. FIG. 1C is an exploded plan view of the device.

FIGS. 2A and 2B show a side view and a plan view, respectively, of the drug storage means used in the device described in FIGS. 1A, 1B, and 1C.

FIGS. 3A and 3B are drawings of a drug dispensing device having a circular configuration. FIG. 3A is a plan view of the device. FIG. 3B is a cross-sectional view of the device.

FIG. 4 is a plan view of the gas canister used in the device described in FIGS. 3A and 3B.

FIGS. 5A and 5B are three-dimensional drawings of the drug delivery device. FIG. 5A shows the device when it is fully-assembled. FIG. 5B is an exploded view of the components of the device.

FIG. 6 is a three-dimensional drawing of the piston assembly.

FIG. 7 is a two-dimensional drawing showing a cross-section of the fully-assembled device.

DETAILED DESCRIPTION OF THE INVENTION

I. Drug Delivery Dispenser Device

The dispenser device is a compact, handheld dispensing device capable of delivering drug dose quantities of aerosolized dry powder particles to any region of the oral cavity and most specifically to the sublingual region of the oral cavity of a patient. The dispenser device may have any suitable shape that is compact and can be handheld. In one embodiment the device has a generally tubular shape. In another embodiment, the device has a generally circular shape. In a third embodiment, the device is generally in the shape of a rectangular box.

A. Tubular Dispenser Device

Figure 1A:
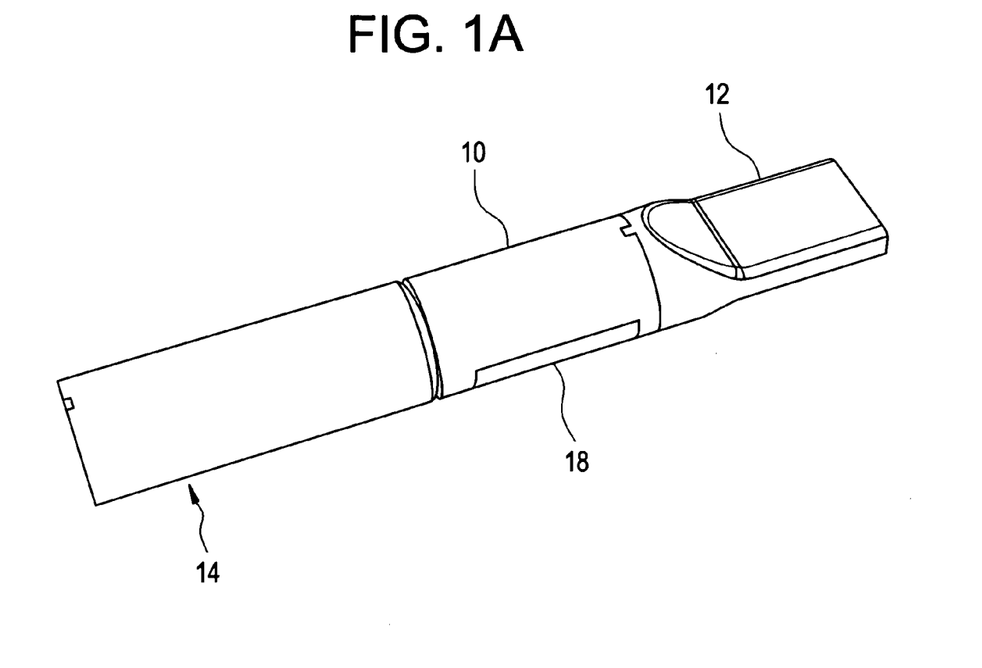
Figure 1B:
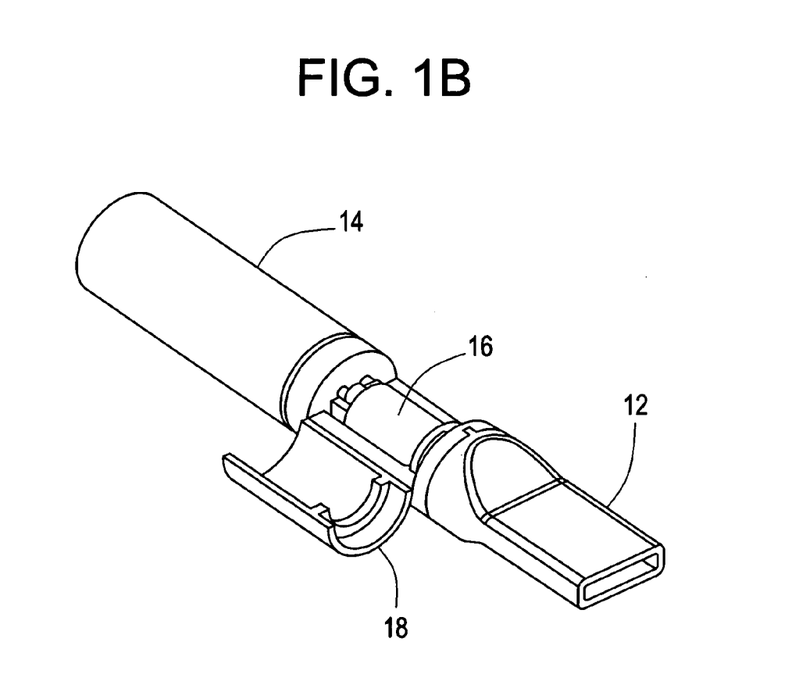
Figure 1C:
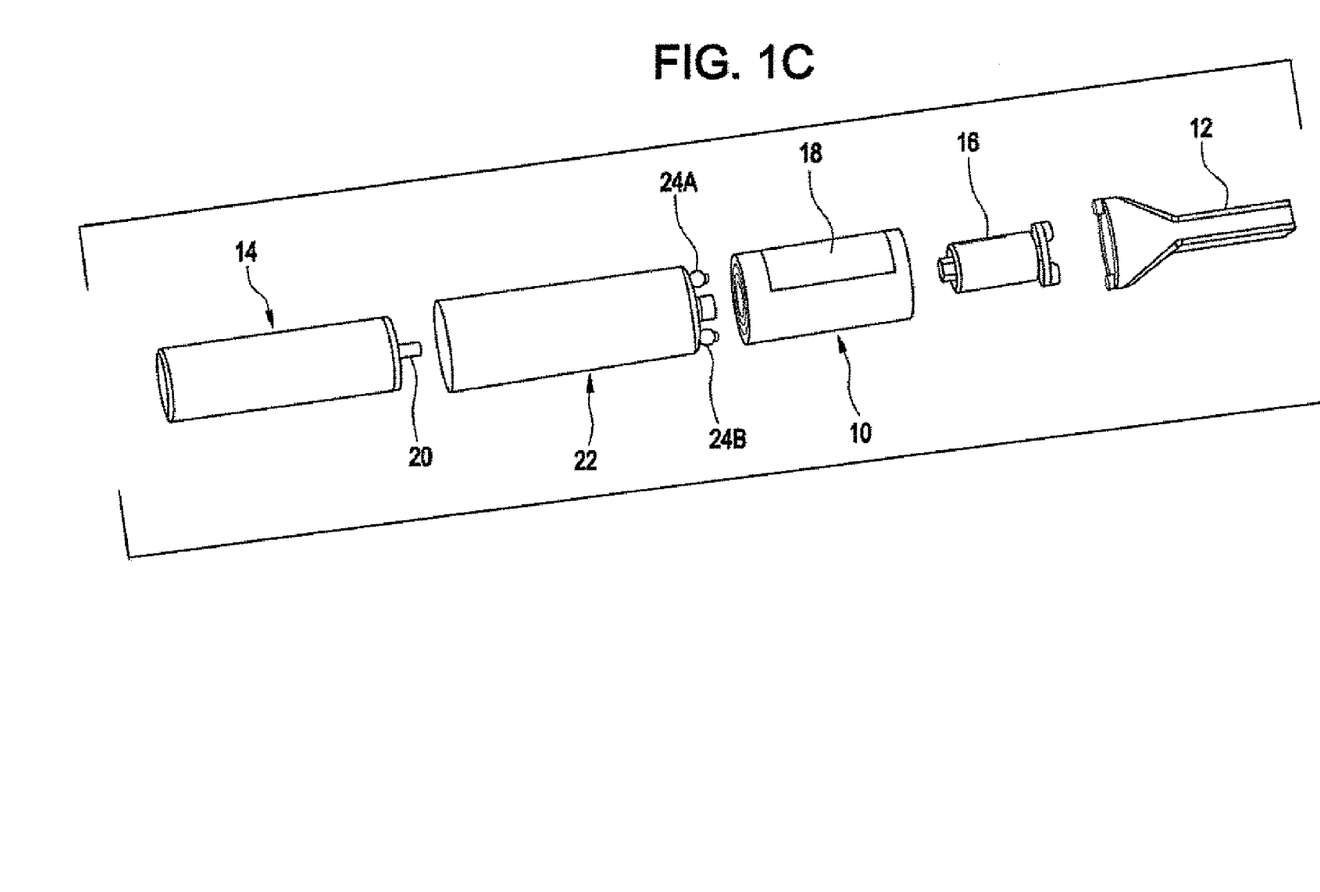

FIGS. 1A, 1B and 1C illustrate a dispenser in a substantially tubular shape with each element in a linear alignment. The device includes a dispenser body (10), a mouthpiece (12), a gas canister (or other means for dispensing a single drug dose) (14), and a drug cartridge (16). In this embodiment, the tubular dispenser device has a diameter generally ranging from 0.25 inches 2 inches, preferably from 0.5 inches to 1.5 inches. The length generally ranges from 2 inches to 7 inches, preferably 30 inches to 5.5 inches.

1. Dispenser Body Housing

The dispenser body (10) is designed to hold all of the elements of the device. The dispenser body is open at both ends. The mouthpiece (12) connects to one end and the drug dispensing means (14) connects to the other end. The dispenser body preferably contains a door (18), which can be opened to insert the drug storage means (16) and closed prior to administration of the drug dose. In a preferred embodiment, the dispenser body includes a means for locking the door in place so that it cannot be opened during drug administration to a patient. Preferably the means for locking the door uses an interlocking device. Suitable interlocking devices include a pin, cam or latch to prevent the door from opening. Another interlocking device contains a channel with an area with a larger opening and an area with a smaller opening. When the mouthpiece is rotated in one position, the door is aligned with the smaller opening in the channel, preventing the door from opening. When the mouthpiece is rotated into a second position, the door is aligned with the larger opening in the channel, allowing the door to open.

2. Mouthpiece

The mouthpiece (12) is attached to one end of the dispenser body (10). The mouthpiece (12) is in linear alignment with the dispenser body (10) and is rotatable about the central axis that runs along the length of the dispenser device. In a preferred embodiment, rotating the mouth piece a predetermined distance (e.g. 45° or 90° around the central axis of the device) around the dispenser body (10) locks the door (18) in the closed position. In the preferred embodiment, the mouthpiece is designed to be placed in the sublingual region of a patient's mouth.

3. Dosage Dispensing Means

Dosage dispensing means can be any means which exerts sufficient directed force to release a single dosage from the dose storage means and expel it from the device to a delivery site in the patient's mouth. Examples include a gas canister or a piston. The gas canister (14) is generally a commercially available canister containing compressed gas. The gas may be any pharmaceutically acceptable inhalable gas or pharmaceutically acceptable propellant. Examples of suitable gases include nitrogen, carbon dioxide, nitrous oxide, and air. The gas canister contains a valve (20). Optionally, the gas canister is placed in a canister casing (22). The canister casing surrounds the gas canister and connects it to the dispenser body. Suitable means for connecting the canister casing to the dispenser body include mating elements (24A and 24B) that protrude from the casing and mate with complementary configured spaces in the dispenser body (10) (not shown in figures). The mating elements may be in any suitable shape, including spheres, squares, etc. When the gas canister is pressed against the end of the dispenser body, the valve is punctured, allowing the gas to flow out of the canister (10) and into the dispenser body (10).

In another embodiment, the dispensing means is a piston which may be manually activated or activated by releasing a catch to allow a spring to force the piston in a desired direction.

4. Drug Cartridge

Figure 2A:
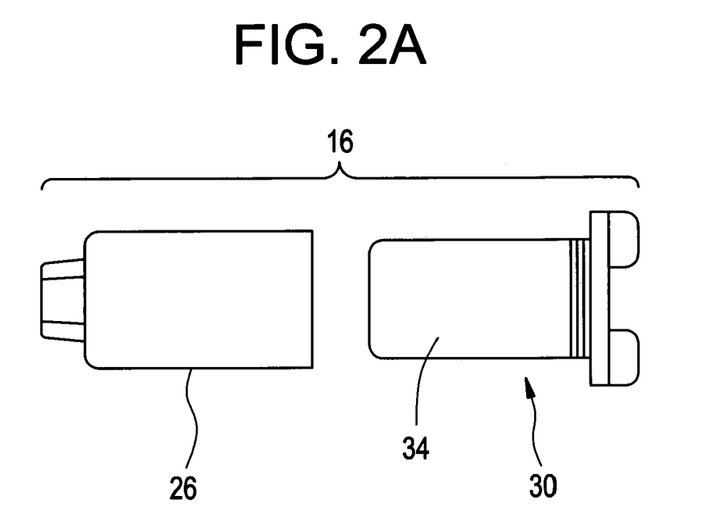
Figure 2B:
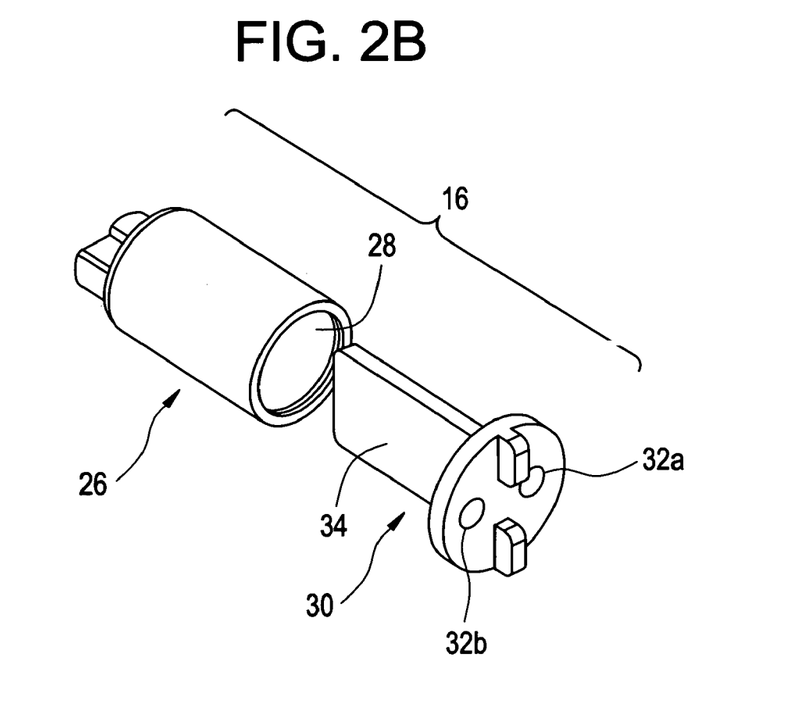

As illustrated in FIGS. 2A and 2B, the drug cartridge (16) contains two main parts. The bottom part (26) of the drug cartridge (16) contains one or more chambers (28) to store the powdered dosage formulation. The top (30) of the cartridge (16) is in rotatable alignment with the bottom part (26) and is able to rotate about the center axis of the drug cartridge. The top of the cartridge contains one or more holes (32A and 32B) that can be aligned with the one or more holes in the bottom portion of the cartridge (holes not shown in figures). The top (30) of the cartridge (16) is placed over the bottom part (26).

In one embodiment, the top (30) of the cartridge (16) contains one or more section dividers (34) which, when placed inside the bottom of the cartridge, divide the cartridge chamber (28) into two or more chambers. In another embodiment, the bottom part (26) of the cartridge (16) contains one or more section dividers which divide the chamber into two or more chambers (not shown in figures). Each chamber contains a hole at the end of the bottom portion distal to the top of the cartridge (holes not shown in figures). Prior to placing the cartridge in the dispenser body (10), the hole(s) at the end distal to the top of the cartridge are covered. The covering may be a material that is punctured upon placement in the dispensing device or the covering may be a removable material, such as an adhesive (e.g. tape) or metallic material. The cartridge is filled with a unit dose of the drug formulation.

In one embodiment, the cartridge has one chamber. In another embodiment, the cartridge contains two chambers, which can be used to separate materials that are not stable when stored together or to separate two drug formulations (see FIGS. 2A and 2B). In still another embodiment, the cartridge contains three or more chambers, which can be used to separate materials that are not stable when stored together or to separate different drug formulations.

B. Circular Dispenser Device

Figure 3A:
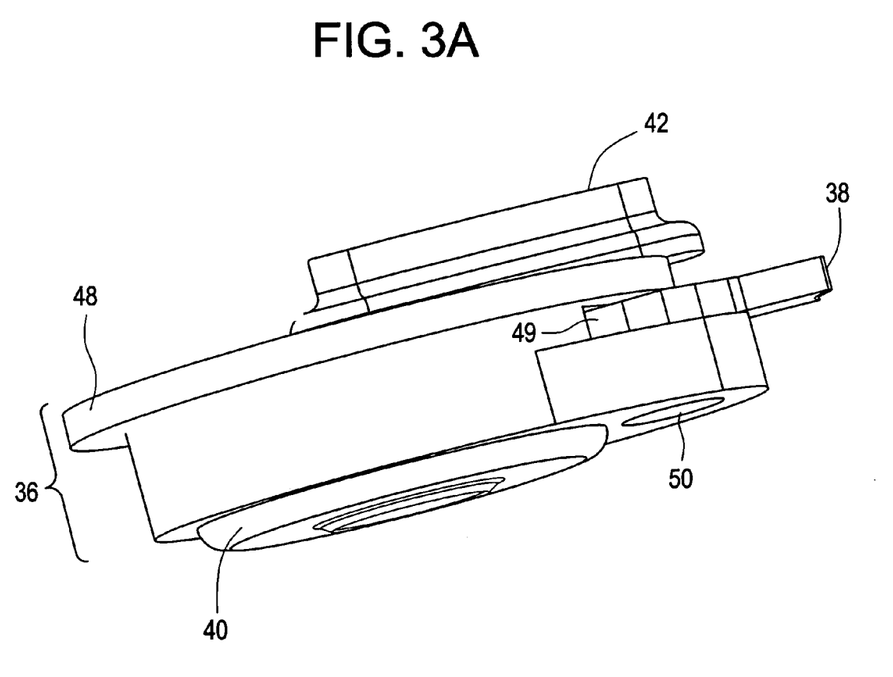
Figure 3B:
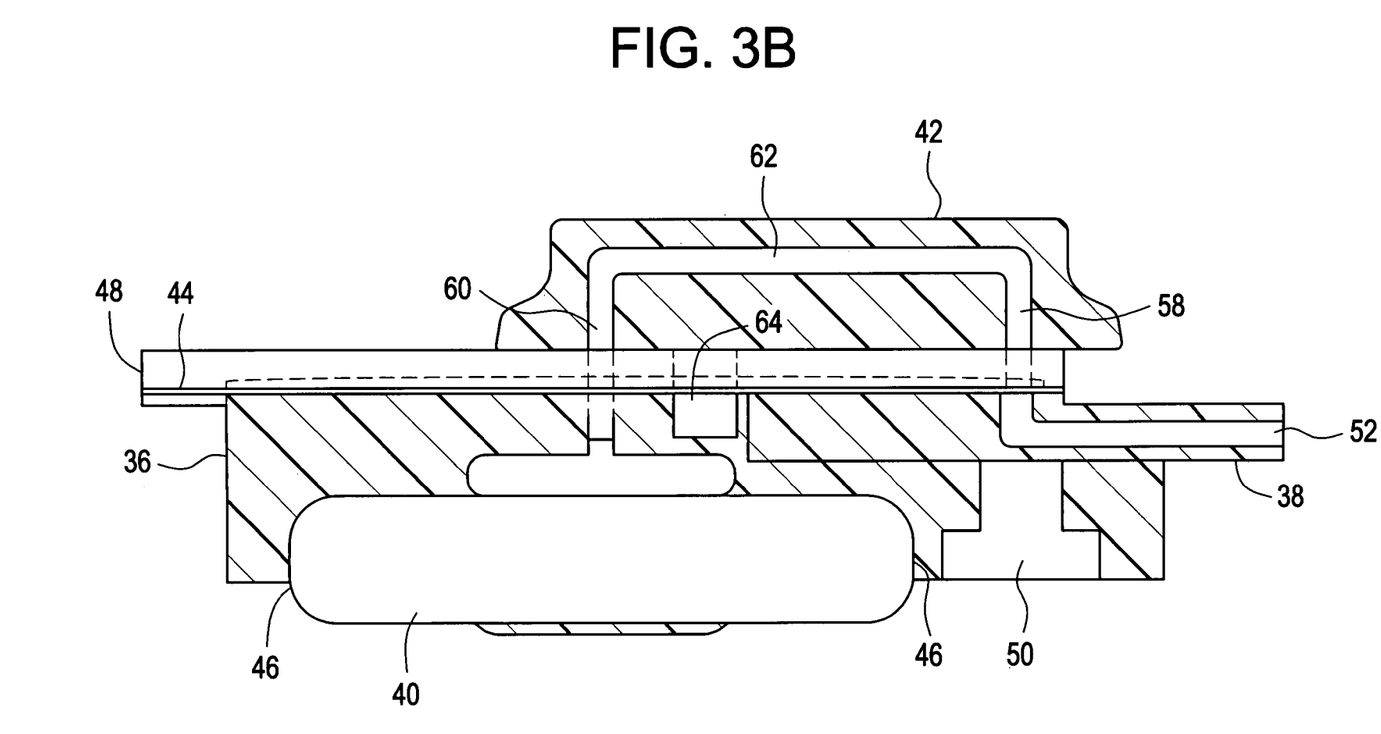

FIGS. 3A and 3B illustrate a dispenser device in a substantially circular shape. The dispenser device contains a means for opening and closing a valve in the dosage dispensing means canister and a means for puncturing the drug storage means such as a blister pack to administer the medicine. In a preferred embodiment, the means for opening and closing the valve is the same component as the means for puncturing the blister pack. In the preferred embodiment, the device contains a dispenser body (36), a mouthpiece (38), a gas canister (40), a plunger arm (42), and one or more drug discs containing blister packs (44). The circular dispensing device has a diameter (measured across the top of the device) generally ranging from 1 inch to 5 inches, preferably ranging from 1.5 inches to 3 inches, most preferably 2.5 inches. The circular dispensing device has a height (or thickness) generally ranging from 0.5 inches to 2 inches, preferably 0.75 inches to 1.5 inches.

1. Dispenser Body

The dispenser body (36) has an opening in the bottom (46) suitable for the placement of the gas canister. The top of the device contains a substantially hollow circle around the perimeter of the device (48), with a hollow center. The hollow circle is designed to contain one or more drug discs containing a plurality of medical powder storage chambers spaced apart from each other in a circumferential direction (also known as "blister packs)". In the preferred embodiment, the hollow circle is designed to contain two discs, where one is place on top of the other. Optionally, the circle may contain two or more drug discs.

In a preferred embodiment, the hollow circle is covered with a flat, circular cover containing one hole in the center, another hole near the center, and a third hole near the perimeter of the circle. The third hole should align substantially with the location of one of the blister packs.

2. Mouthpiece

The mouthpiece (38) is attached to the dispenser body (36). In the preferred embodiment, the mouthpiece (38) rotates from a closed position suitable for storage of the device (49) in the dispenser body to an open position, protruding outside of the dispenser body (FIGS. 3A and 3B show the mouthpiece in the open position). As shown in FIGS. 3A and 3B, the mouthpiece may be attached to a cylinder (50) to allow the mouthpiece to rotate about the cylinder. The mouthpiece contains a hollow conduit (52) which allows for the gas and powdered drug formulation to flow out of the device and into the patient's mouth. In the preferred embodiment, the hollow conduit is configured to mix, disperse, and aerosolize the powdered drug formulation.

In the preferred embodiment, the mouthpiece is designed to be placed in the sublingual region of a patient's mouth.

3. Drug Dispensing Means

Figure 4:
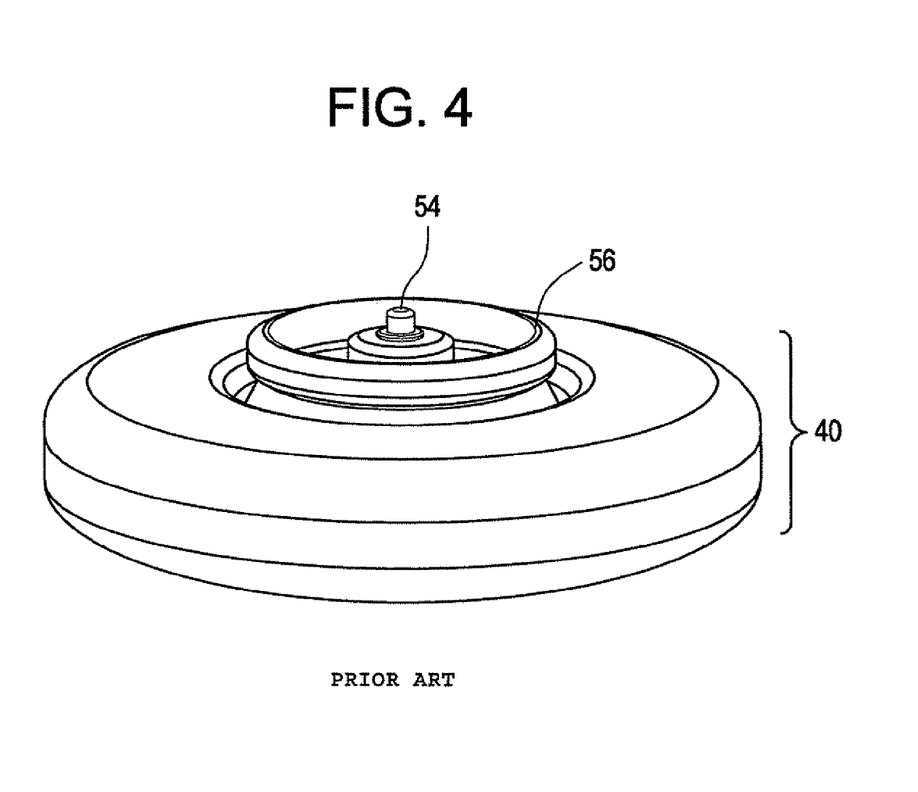

The drug dispensing means are the same or similar to those discussed above. Gas canister (40) shown in FIG. 4 is a commercially available circular canister containing compressed gas. The gas may be any pharmaceutically acceptable inhalable gas or pharmaceutically acceptable propellant. One manufacturer of a suitable gas canister is 3M. The gas canister contains a gas outlet (54) and an outer rim (56). The gas canister also contains a valve for releasing the gas. The valve opens when the outer rim is pressed and closes in the absence of pressure to the outer rim.

4. Dosage Dispensing Means

The dosage dispensing means can be as discussed above. In one embodiment, the plunger arm (42) is located on top of the dispenser body. In a first area proximal to the mouthpiece, the plunger arm (42) contains at least one hollow tube (58) with a diameter substantially the same as the diameter of a blister pack. This cylinder is aligned with the mouthpiece and at least one blister pack. Optionally, the plunger arm contains more than one hollow cylinder proximal to the mouthpiece. This embodiment is particularly useful to administer drug formulations from a drug disc containing two or more radially aligned blister packs. In this embodiment, the number of hollow tubes is preferably the same as the number of blister packs in radial alignment.

At the opposite end of the plunger arm, in an area distal to the mouthpiece and proximal to the center of the dispensing device, the plunger arm contains another hollow tube (60) that connects to the gas outlet (54). In the preferred embodiment, this cylinder has a slightly larger diameter than the gas outlet (54) so that the gas outlet (54) fits inside the hollow tube (60).

The plunger arm also contains a conduit (62) that connects the hollow tube (60) proximal to the center of the device with the hollow tube (58) proximal to the mouthpiece (38).

In one embodiment the plunger arm acts as a lever, with the fulcrum in the center of the device. In this embodiment, when the plunger arm is pushed down in the area proximal to the mouthpiece, the plunger arm is raised up in the center, pulling the gas outlet (54) up, thereby pushing in the outer rim (58) and opening the valve inside the gas canister (not shown in figures).

In the preferred embodiment, the plunger arm also contains a protrusion (64). When the gas canister is placed in the dispenser body, the gas outlet (54) aligns with the hollow tube in the center of the dispenser body (60) and the outer rim (56) is beneath the protrusion (64). When the gas outlet (54) is pulled up and/or the outer rim (58) is pressed by the protrusion (64), a valve inside of the gas canister (not shown in FIG. 4) is opened and the gas flows out of the canister through the gas outlet (54).

The protrusion (64) has a length suitable to fit inside the dispenser body and above the outer rim (56) and to touch the outer rim (56) only when the plunger arm is depressed. Suitable sizes range from 0.125 to 1 inch, preferably from 0.25 inches to 0.375 inches, most preferably up to 0.375 inches. The protrusion may have any shape that fits within the size range, including cylinder, oval, squares and circle. The protrusion may be hollow or solid.

To release and administer the drug formulation, the patient pushes the plunger arm down. This motion results in puncturing the one or more blister packs located beneath the one or more tubes (58) in the area proximal to the mouthpiece (38) and empties their contents into the hollow tube (52) in the mouthpiece (38). Simultaneously, the valve in the canister opens and the gas flows out the canister outlet (54), through the hollow tube (60) proximal to the center of the dispenser device, through the conduit (62) in the plunger arm (42), through the hollow tube (58) proximal to the mouthpiece (38), and into the tube (52) in the mouthpiece (38). When the gas flows through the hollow tube (58) proximal to the mouthpiece (38) and into the tube (52) in the mouthpiece (38), it pushes the drug formulation out of the device and into the patient's mouth.

5. Drug Discs

The dispenser device may contain one or more replaceable drug discs. The drug discs contain a plurality of storage chambers (also known as blister packs) arranged in a circle, preferably along the circumference of the circle. Each of the storage chambers is sealed by a breakable wall and holds a unit-dose of medication. A patient gains access to the medication in a given chamber by puncturing the breakable wall associated with the storage chamber with the hollow tube (58) proximal to the mouthpiece (38).

In another embodiment, one drug disc may contain two or more blister packs aligned radially around the circumference of the disc. This arrangement can also be used for two or more blister packs that can be combined to deliver a single dose or the drug formulation.

The one or more drug discs are rotatably mounted inside the hollow circle (48) on the perimeter of the dispenser body (36). In one embodiment, each of the storage chambers contains a unit dose of the drug formulation. Alternatively, one or more the storage cells may be combined to administer a single dose of the drug formulation.

C. Rectangular Dispenser Device

Figure 5A:
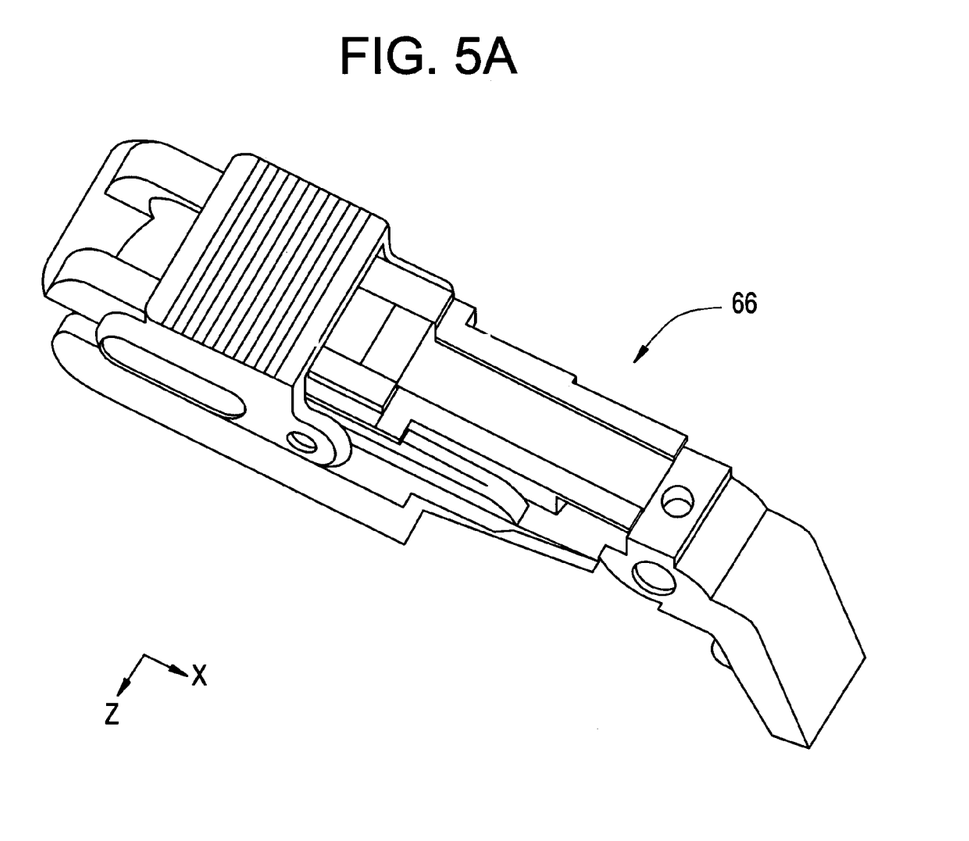
Figure 5B:
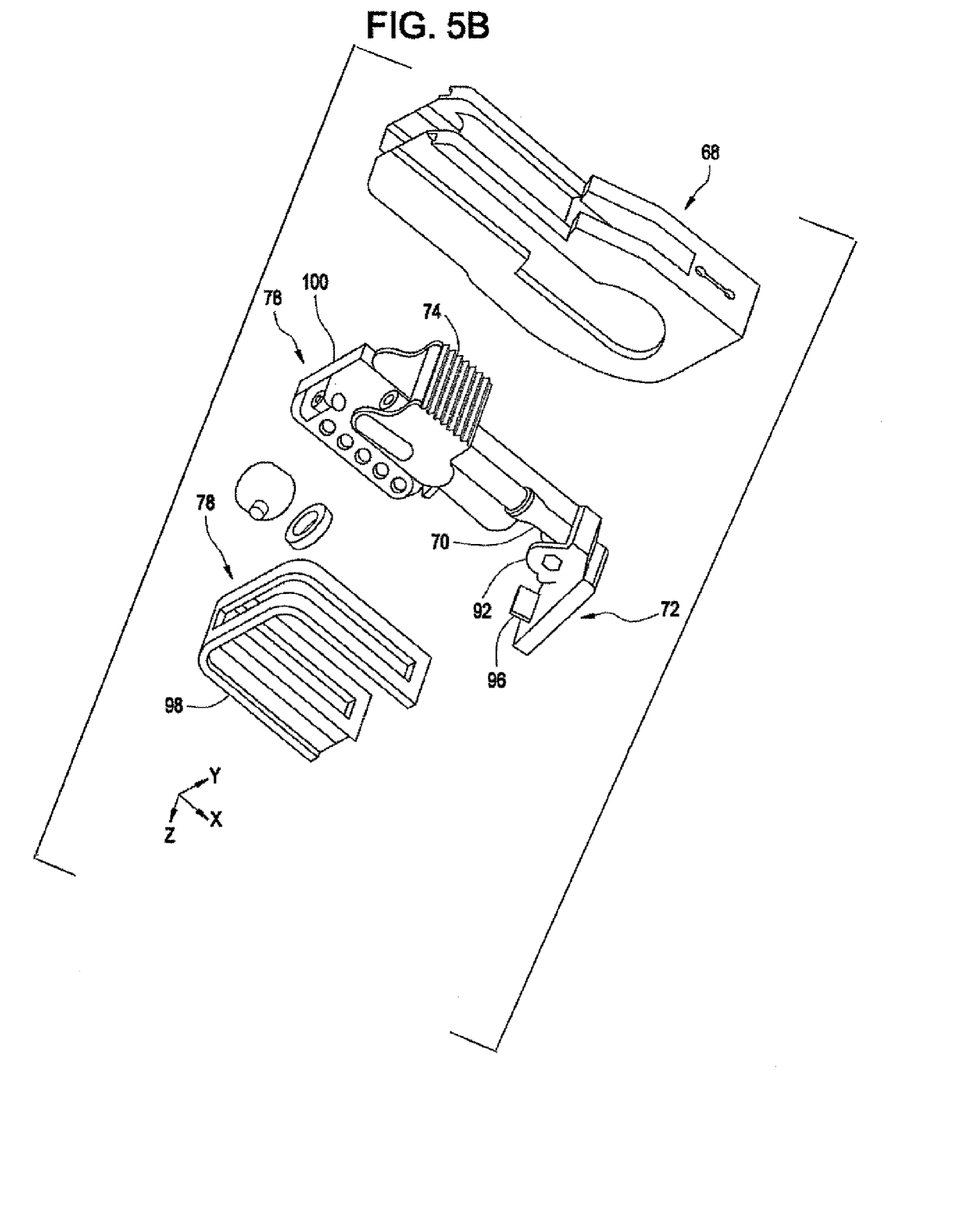

As shown in FIGS. 5A and 5B, the generally rectangular dispenser device, may be a piston-containing device (66). This device contains six core subassemblies: the main housing (68) and peripheral fasteners, the piston assembly (70), the rotary mouthpiece assembly (72), the cocking mechanism assembly (74), the firing mechanism assembly (76), and the drug dose storage magazine assembly (78). The rectangular dispenser device generally has a length (measured across the top of the device, along the cocking mechanism, with the mouthpiece in the closed position) ranging from 1.5 inches to 6 inches, preferably 2.5 inches to 4 inches. The rectangular dispenser device generally has a height generally ranging from 1.5 inches to 6 inches, preferably from 2 inches to 4 inches. The rectangular dispenser device generally has a depth generally ranging from 0.5 inches to 2 inches, preferably from 0.75 inches to 1.5 inches, most preferably up to 1 inch.

1. The Main Housing

As shown in FIG. 5B, the main housing (68) is the central attachment member for all of the dispensing device subassemblies and also serves as a protective housing, and hand orientation-operation guide. The main housing may be fabricated from a number of materials but in the preferred embodiment from polycarbonate material.

2. The Piston Assembly

Figure 6:
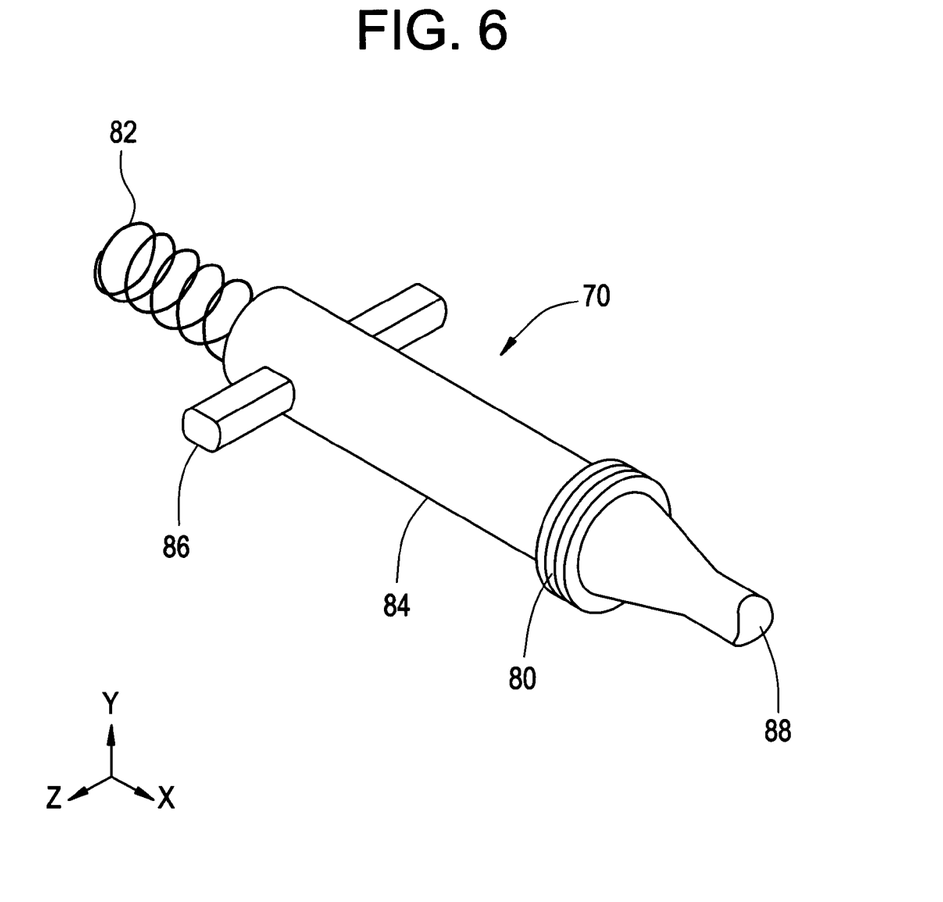

As shown in FIG. 6, the piston assembly (70) is a pneumatic-charged piston assembly, which contains (i) an o-ring (80), which is used for initial testing only, (ii) a compression-charge spring (82), (iii) a piston-member (84), (iv) a piston-guide bearing (86), and (v) a piston-head end cap (88). The spring-size and spring-constant can be determined by equating the piston-force ($F_p$) to the spring-force ($F_s$). The piston-force is calculated by multiplying the piston mass ($m_p$) by the stroke acceleration ($a_s$) as shown in Equation 1.

$$F_p = m_p \times a_s \tag{Eq. 1}$$

The spring-force ($F_s$) is calculated by multiplying the displacement by the spring (d) by the spring constant ($C_s$) as shown in Equation 1.

$$F_s = d \times C_s \tag{Eq. 2}$$

By equating the piston-force ($F_p$) to the spring-force ($F_s$), and then solving for acceleration ($a_s$) or the spring-constant ($C_s$), one can determine the optimum piston fluidics for the dispensing system. The piston bore and stroke can also be calculated for optimum drug powder aerosolization and delivery.

Optionally, the piston assembly can be substituted with a pneumatic "gas-charged" cylindrical tank.

3. Rotary Mouthpiece Assembly

Figure 7:
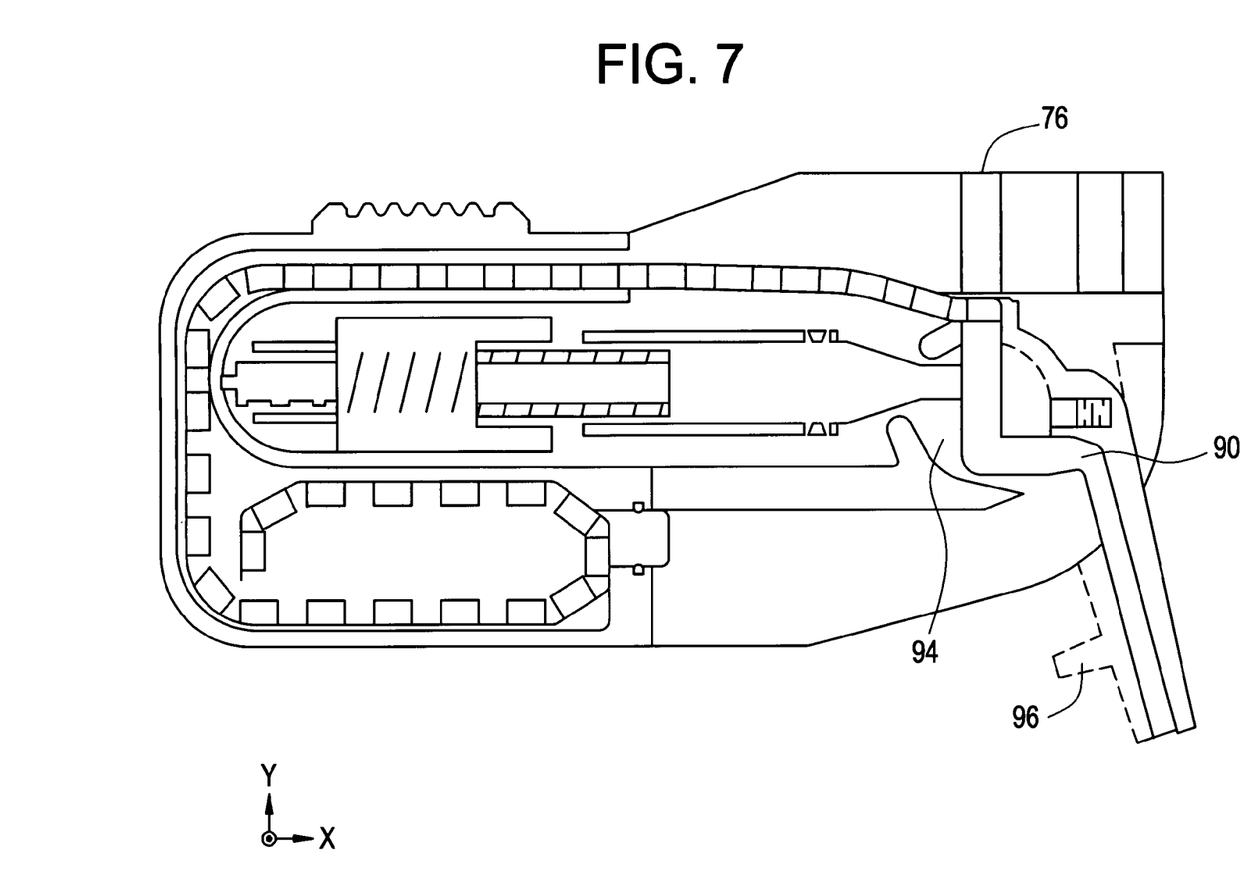

As shown in FIGS. 5A and 7, the rotary mouthpiece assembly (72) has a convoluted ducting design (90) that slows down the gas velocity and converts a portion of the kinetic energy into particle mixing energy (vortex-eddies). In the preferred embodiment, this configuration incorporates the de-agglomeration, mixing, and dispersion mechanics necessary for low-velocity aerosolization of slightly cohesive, large granule, particle powders. In addition, the mouthpiece has a spring and ball detent mechanism (92) to positively locate it in a stowed or deployed position. The mouthpiece is configured so that the dispersion (firing) chamber (94) of the dispenser is covered when the mouthpiece is stowed away. The mouthpiece can mechanically cog-forward the next loaded drug dose tab when it is placed in the stowed position. Optionally, the drug dose tab can be fed manually by a separate feed mechanism.

The tab (96) on the underside of the mouthpiece is used to position the mouthpiece at an optimum distance and an optimum angle to deliver to a desired region of the oral cavity. When a patient uses the device, the tab (96) is placed touching and parallel to the two front incisor teeth of the patient's lower jaw. The distance of the tab from the distal end of the mouthpiece and the angle the mouthpiece makes with the tab is optimized to dispense a dry powder formulation to the sublingual region. By adjusting the angle and the distance of the tab from the distal end of the mouthpiece, one can optimize delivery to any area of the oral cavity, including the upper pallet or the back of the throat.

4. The Cocking Mechanism Assembly

The cocking mechanism assembly (74) is a user-friendly pinch-type, i.e. thumb and forefinger, or thumb-only pull-bar that compresses the compression-charge spring (82) for pneumatic pressure, discharge firing. The cock-bar member tracks in one linear rail direction along the axis of the piston compression spring. If the pneumatic piston-accumulator assembly is substituted with a pre-charged component, the cocking mechanism assembly can alternatively be used as a gas cylinder loading and locking member.

5. Firing Mechanism Assembly

The firing mechanism assembly (76) is a complex agglomeration of inter-connecting parts. This mechanism loads the powder dose by breaking through the blister dose tab, then moves the powder dose to the dispersion or "firing chamber", cuts-off the dose tab from the dose tab ribbon feed, and triggers the cocking mechanism assembly (74) to release the compressed compression-charge spring (82).

6. Drug Dose Storage Magazine Assembly

The drug dose magazine (78) assembly is composed of the magazine housing (98) and the drug dose ribbon with feed-leader strip (100). The ribbon can contain a plurality of two side-by-side dose tabs, which are simultaneously loaded and dispensed within the same "firing chamber". Alternatively, the ribbon may contain a dose tab on only one side of the ribbon. Thus the dispenser can deliver one drug composition or two drug compositions (or two doses of the same drug composition) simultaneously. Further, the ribbon can be used to administer two parts of a drug formulation that are unstable when stored together, but stable when stored separately. The dose tab ribbon is slot connected so that it can be cog-fed forward. Optionally, each tab can be cut-off by a shear blade after use.

II. Drug Formulations

The drug formulations that are administered to a patient using the drug dispensing device are preferably in the form of a dry powder. The powder may consist of drug only, drug plus surfactant or other excipient, or drug plus polymer and other excipients. Drug particles are preferably less than 100 microns in diameter, more preferably less than 50 microns, most preferably less than 10 microns. These may be prepared by any standard technology including spray drying and lyophilization and grinding.

This form provides many advantages over other forms. By formulating the drug as a dry powder, the long term stability or shelf life of the drug is markedly increased. It is also easier to sterilize/sanitize a dry powder initially and to maintain a sanitary sterile condition over an extended period of time. Two or more substances that would not be compatible in a liquid formulation can be stored together compatibly as a dry powder.

One or more substances can be stored and administered using the drug dispensing devices described herein. Thus, for two or more substances that cannot be stored together, even as a dry powder, they can be stored separately, in different blister packs, separate compartments in a drug cartridge, or different tabs that are side-by-side on the drug dose ribbon, and delivered simultaneously.

III. Methods of Using the Devices

The drug delivery device is used to administer powdered drug compositions to the oral cavity, and is particularly useful for sublingual drug delivery.

A. Tubular Dispenser Device

The drug cartridge may be available as a single cartridge or as a part of a cartridge assembly. In the preferred embodiment, the cartridge is part of a cartridge assembly. To use the tubular device a single drug cartridge (16) is removed from a cartridge assembly. Then the covering is removed from the bottom of the cartridge to open the bottom of the cartridge. Then the door (18) in the dispenser body is opened, and the cartridge is placed in the open area of the dispenser body, with the top (30) of the cartridge (16) proximal to the mouthpiece and the holes in the bottom part (26) of the cartridge proximal to the gas canister (14). Then the door (18) in the dispenser body is closed. Next a patient rotates the mouthpiece a predetermined distance (e.g. 45° or 90° wound the central axis of the device) in the clockwise or counterclockwise direction to align the one or more holes (e.g. 32A and 32B on the top of the cartridge with the one or more holes on the bottom part (26) of the cartridge (not shown in figures). In a preferred embodiment, the dispenser body locks the door in the closed position, when the mouth piece is rotated the predetermined distance. The holes are also aligned with the mouthpiece outlet. Then the dispenser is placed under the patient's tongue. Finally, the gas cartridge is pressed into the end of the dispenser body that is proximal to the cartridge. This opens the gas cartridge, releasing the compressed gas into the dispenser body and through the hole(s) in the drug cartridge. As the gas travels through the drug cartridge, it aerosolizes the powdered drug formulation and pushes it out of the drug cartridge and into the mouthpiece and administers the contents of the cartridge into the oral cavity, most preferably the sublingual area or buccal area. In the preferred embodiment, all of the powdered formulation in the drug cartridge is administered to the patient in a single use.

The dispenser then is removed from the mouth. To remove the empty cartridge, the dispenser body is rotated a predetermined distance in the opposite direction, the door opened and the cartridge removed. The door is then closed and the device stored until the next use, preferably in the absence of drug.

B. Circular Dispenser Device

To use the circular shaped device to administer the powdered drug formulation, first, one or more drug discs are placed inside the hollow circle (48) on the perimeter of the dispenser body (36) and one or more of the blister packs are aligned with the mouthpiece. For example, if two drug discs are used, one drug disc is placed on top of the other and both are aligned so that one blister pack in the first disc is directly on top of one blister pack in the second disc and both blister packs are aligned with the mouthpiece. This arrangement can also be used for three or more drug discs. In another embodiment, one drug disc is used and the drug is contained in two or more blister packs aligned radially around the circumference of the disc. The two or more blister packs or two or more drug discs can be combined to deliver a single dose of the drug formulation or to administer two or more drug formulations simultaneously.

Second, the patient presses down the plunger arm (42) to puncture the blister pack(s) with the hollow tube(s) (58) proximal to the mouthpiece (38) and to release the compressed gas from the gas canister (40).

Under these conditions, gas flow directed from the gas canister and into the mouthpiece aerosolizes the powder and pushes the powder contained in the one or more blister packs into the patient's mouth, preferably into the sublingual area. In the preferred embodiment, all of the powdered drug formulation in the punctured blister pack(s) is delivered to the patient.

In order to reuse the device to deliver another dosage of medication, the drug disc(s) is rotated by a predetermined angle, and then the next blister pack is aligned with the mouthpiece. Thus, it is possible to consecutively dose a patient with a specified amount of medical powder by rotation of the drug disc without removing the drug disc or replacing the gas cartridge.

C. Rectangular Dispenser Device

To use the rectangular shaped device, a patient opens the device, places the tab (96) parallel to the two front incisor teeth of the patient's lower jaw, so that it touches these teeth. Then the patient pulls back the cocking mechanism to compress the piston assembly, and when the patient is ready to administer the drug, the patient simply triggers the firing mechanism assembly, such as by pushing on a pin, which results in release of the drug powder dose tab and the release of the piston, thereby mixing the powdered drug with the air and delivering the aerosolized drug through the mouthpiece to the patient's oral cavity.

By delivering a dry powder aerosol to the oral cavity, it is possible to cover a large surface area in the oral cavity, thereby increasing absorptive surface and as a consequence increase bioavailability. Additionally, the device can uniformly cover an irregular and variegated surface. As a fine dry powder coating, the drug is kept in contact with the absorptive surface for much longer periods of time without the urge to swallow.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention. Those skilled in the art will recognize, or be able to ascertain using no more than routine experimentation, many equivalents to the specific embodiments of the invention described herein. Such equivalents are intended to be encompassed by the following claims.

We claim:

1. A dry powder drug delivery device for administration of a powdered drug formulation to the sublingual region of the oral cavity, comprising
    a dispenser body housing,
    a mouthpiece comprising a distal end, a proximal end and a portion defining a hollow conduit, wherein the distal end is configured for insertion into the sublingual region of the oral cavity of a human, wherein the hollow conduit comprises a first opening at the distal end of the mouthpiece and a second opening at the proximal end of the mouthpiece, and wherein the opening at the distal end of the mouthpiece is smaller than the opening at the proximal end of the mouthpiece, wherein the hollow conduit mixes, disperses, directs, and aerosolizes the powdered drug formulation in use,
    a chamber configured for the placement of one or more drug dosage storage means selected from the group consisting of drug cartridges, drug discs, drug dose ribbons and drug blister packs,
    means for opening the one or more drug dosage storage means, and
    means for dispensing a dosage from the one or more drug dosage storage means into the proximal end of the mouthpiece with sufficient force for the dosage to travel through the hollow conduit and out of the opening at the distal end of the mouthpiece, wherein the means for dispensing a dosage is selected from the group consisting of a gas canister and spring piston.

2. The drug delivery device of claim 1 further comprising one or more drug dosage storage means selected from the group consisting of a drug cartridges, drug blister packs, drug discs, and a drug dose ribbons.

3. The drug delivery device of claim 1 wherein the housing has a configuration selected from the group consisting of circular configurations, tubular configurations, and rectangular configurations.

4. The device of claim 1, wherein the the hollow conduit alters the velocity and trajectory of a gas flowing through the mouthpiece in use.

5. The device of claim 1 comprising a protrusion on the underside of the mouthpiece that positions the mouthpiece at a selected distance and angle to deliver a drug to the sublingual region of the oral cavity.

6. The device of claim 1 wherein the drug dosage storage means is a cartridge and the cartridge comprises one or more storage chambers rotatable about a center axis of the cartridge.

7. The device of claim 6 further comprising section dividers within the cartridge.

8. The device of claim 6 further comprising openings in the cartridge having coverings which are punctured by the means for opening the drug cartridge.

9. The device of claim 1 comprising a circular dispenser body housing.

10. The device of claim 9 wherein the mouthpiece is attached to the dispenser body, wherein the mouthpiece rotates from a closed position suitable for storage of the mouthpiece in the dispenser body to an open position, protruding outside of the dispenser body.

11. The device of claim 1 further comprising a drug dose ribbon.

12. The device of claim 11, wherein the drug dose ribbon comprises drug dose tabs on both sides of the drug dose ribbon.

13. The device of claim 1 comprising a plunger arm located on top of the dispenser body housing, wherein the plunger arm comprises a first hollow tube, a second hollow tube, and a conduit, wherein the conduit connects the first hollow tube with the second hollow tube, and wherein the first hollow tube has a diameter substantially the same as the diameter of a blister pack, wherein the first hollow tube is aligned with the second opening at the proximal end of the mouthpiece and at least one blister pack when placed in the chamber.

14. The device of claim 13 wherein the second hollow tube is connected to a gas canister for dispensing drug from a blister pack pierced by the first hollow tube.

15. The device of claim 1 comprising a circular drug disc, the disc comprising radially aligned blister packs, wherein the disc is rotatably mounted within the dispenser body housing.

16. The device of claim 1 comprising peripheral fasteners, a piston assembly, a rotary mouthpiece assembly, a cocking mechanism assembly, and a firing mechanism assembly, wherein the chamber is configured for the placement of a drug dose storage magazine assembly.

17. The device of claim 16 further comprising a drug dose ribbon.

18. A method of administering a drug to the sublingual region of the oral cavity of a person in need thereof comprising providing a drug delivery device in combination with a dry powdered drug formulation, wherein the device comprises a dispenser body housing, a mouthpiece comprising a distal end, a proximal end and a portion defining a hollow conduit, wherein the distal end is configured for insertion into the sublingual region of the oral cavity of a human, wherein the hollow conduit comprises a first opening at the distal end of the mouthpiece and a second opening at the proximal end of the mouthpiece, and wherein the opening at the distal end of the mouthpiece is smaller than the opening at the proximal end of the mouthpiece, wherein the hollow conduit mixes, disperses, directs, and aerosolizes the powdered drug formulation, drug dosage storage means for one or more drug cartridges, drug discs, drug dose ribbons or drug blister packs, means for opening one or more drug cartridges, drug discs, drug dose ribbons, or blister packs, and means for dispensing a dosage from the drug dosage storage means into the proximal end of the mouthpiece with sufficient force for the dosage to travel through the hollow conduit and out of the opening at the distal end of the mouthpiece, wherein the means for dispensing a dosage is selected from the group consisting of a gas canister and spring piston, inserting the distal end of the mouthpiece in the sublingual region of the person's mouth, and administering the dry powdered drug formulation to the sublingual region of the oral cavity of the person.

* * * * *

UNITED STATES PATENT AND TRADEMARK OFFICE
CERTIFICATE OF CORRECTION

| | | |
|---|---|---|
| PATENT NO. | : 7,658,721 B2 | Page 1 of 1 |
| APPLICATION NO. | : 11/037737 | |
| DATED | : February 9, 2010 | |
| INVENTOR(S) | : Steiner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 859 days.

Signed and Sealed this

Thirtieth Day of November, 2010

David J. Kappos
*Director of the United States Patent and Trademark Office*